United States Patent [19]
Bell et al.

[11] Patent Number: 5,225,609
[45] Date of Patent: Jul. 6, 1993

[54] PRODUCTION OF TERTIARY ALKYL ETHER USING IMPROVED ZEOLITE CATALYST

[75] Inventors: Weldon K. Bell, Pennington; Werner O. Haag, Lawrenceville, both of N.J.

[73] Assignee: Mobil Oil Corporation, Fairfax, Va.

[21] Appl. No.: 808,496

[22] Filed: Dec. 17, 1991

[51] Int. Cl.$^5$ .............................................. C07C 41/05
[52] U.S. Cl. .................................................. 568/697
[58] Field of Search ........................................ 568/697

[56] References Cited

U.S. PATENT DOCUMENTS

| | | |
|---|---|---|
| 4,605,787 | 8/1986 | Chu . |
| 4,714,787 | 12/1987 | Bell . |
| 4,886,918 | 12/1989 | Sorensen et al. ............... 568/697 |
| 4,962,239 | 10/1990 | Bell et al. ............... 568/697 |

FOREIGN PATENT DOCUMENTS 0055045  12/1984  European Pat. Off. .

*Primary Examiner*—Howard T. Mars
*Attorney, Agent, or Firm*—Alexander J. McKillop; Malcolm D. Keen; L. G. Wise

[57] ABSTRACT

A process is disclosed for the production of alkyl tertiary alkyl ether from alkanol and iso-olefin employing zeolite catalyst, particularly zeolite Beta, that results is a high ether selectivity and a significant reduction in the formation of olefin oligomer by-product. The improvement is realized by incorporating a catalyst pretreatment step in the overall etherification process. The zeolite catalyst pretreatment comprises either steaming or a hydrothermal treatment using liquid water at elevated temperature. The process is particularly effective in reducing the formation of dimer by-product in the zeolite Beta catalyzed process for the formation of MTBE with high selectivity.

28 Claims, No Drawings

PRODUCTION OF TERTIARY ALKYL ETHER USING IMPROVED ZEOLITE CATALYST

This invention relates to the production of high octane alkyl tertiary alkyl ethers. In particular, the invention relates to the production of methyl tertiary butyl ether (MTBE) and methyl tertiary amyl ether (TAME) by a process employing a pretreated zeolite Beta catalyst which reduces the formation of olefin oligomer by-product.

BACKGROUND OF THE INVENTION

It is well known that isobutylene may be reacted with methanol over an acidic catalyst to provide methyl tertiary butyl ether (MTBE) and isoamylenes may be reacted with methanol over an acidic catalyst to produce tertiary amyl methyl ether (TAME). The reaction is a useful preparation for these valuable gasoline octane enhancers and is typical of the reaction of the addition of lower alkanol to the more reactive tertiary alkenes, or iso-olefins, of the type $R_2C=CH_2$ or $R_2C=CHR$ under mild conditions to form the corresponding tertiary alkyl ethers. The feedstock for the etherification reaction may be taken from a variety of refinery process streams such as the unsaturated gas plant of a fluidized bed catalytic cracking operation containing mixed light olefins, preferably rich in isobutylene and isopentenes or isoamylene.

Generally, it is known that asymmetrical $C_5$-$C_7$ alkyl tertiary alkyl ethers are particularly useful as octane improvers for liquid fuels, especially gasoline. MTBE, ethyl t-butyl ether (ETBE), isopropyl t-butyl ether (IPTBE) and TAME are known to be high octane ethers The article by J. D. Chase, et al., *Oil and Gas Journal*, Apr. 9, 1979, discusses the advantages one can achieve by using such materials to enhance gasoline octane. The blending octane numbers of MTBE when added in an amount of 10% to a typical unleaded gasoline are: RON is 118, MON is 101, R+M/2 is 109. Increasing demand for high octane gasolines blended with high octane ethers as octane boosters and supplementary fuels has created a significant demand for these ethers, especially MTBE and TAME.

The production of alkyl tertiary alkyl ethers is known to be catalyzed by Lewis acids such as $AlCl_3$ and $BF_3$, mineral acids and strong organic acids. The reaction equilibrium favors the formation of ether at low reaction temperature, but reaction kinetics at low temperature limits the degree of conversion. In practice, this limitation can be overcome by carrying out the reaction using an excess of either the alkanol or iso-olefin reactant. When excess alkanol is used conversions of iso-olefin above ninety percent are realized. But using excess alkanol results in difficult and costly operations to remove unreacted alkanol from the reaction products. On the other hand, employing an excess of olefin favors the formation of undesirable reaction by-products, such as olefin dimer.

In U.S. Pat. No. 4,605,787 to Chu, incorporated herein by reference, a process is disclosed for the preparation of alkyl tert-alkyl ethers using acidic zeolite catalyst, including zeolite Beta. It has been found that zeolite catalyst suppresses the formation of diisobutylene by-product in the production of MTBE from isobutylene.

In EP 0,055,045 to Daniels a process is disclosed for the production of MTBE using zeolite Beta catalyst. The process employs a large excess of methanol and achieves a conversion of isobutene of about 87 mole % with high selectivity to MTBE.

It is well known that zeolite catalysts, including zeolite Beta, are highly effective under a broad range of conditions for the conversion of oxygenates, such as methanol, to olefins as well as for the oligomerization of olefins to higher molecular weight hydrocarbons. Therefore, it is not altogether unexpected that, even under the relatively mild conditions used for the production of alkyl tert-alkyl ether in contact with zeolite catalyst, some olefin oligomerization would take place with the consequent production of undesirable by-product. In order to fully realize the potential of zeolite Beta catalysis in the production of high octane tertiary ethers, particularly MTBE, there is a need to provide a means to reduce the formation of olefin oligomer by-product.

It is an objective of the present invention to provide a process for the improved production of alkyl tertiary alkyl ether using zeolite catalyst.

A specific objective of the present invention is to provide a process for the improved production of alkyl tertiary alkyl ether using zeolite Beta catalyst.

Another objective of the present invention is to provide a process for the improved production of alkyl tertiary alkyl ether using zeolite Beta catalyst while reducing the formation of olefin oligomer by-product.

SUMMARY OF THE INVENTION

A process has been discovered for the production of alkyl tertiary alkyl ether from alkanol and iso-olefin employing zeolite catalyst, particularly zeolite Beta, that results in a high ether selectivity and a significant reduction in the formation of olefin oligomer by-product. The improvement is realized by incorporating a catalyst pretreatment step in the overall etherification process. The zeolite catalyst pretreatment comprises either steaming or a hydrothermal treatment using liquid water at elevated temperature. The process is particularly effective in reducing the formation of dimer by-product in the zeolite Beta catalyzed process for the formation of MTBE with high selectivity.

More particularly, a process has been discovered for reducing the formation of olefinic by-products in the production of high octane alkyl tertiary alkyl ether using untreated zeolite Beta catalyst particles comprising: steaming or hydrothermally treating the zeolite Beta catalyst particles at elevated temperature; and contacting alkanol and a hydrocarbon feedstream rich in iso-olefins with the steamed or hydrothermally treated catalyst particles under iso-olefin etherification conditions, whereby alkyl tertiary alkyl ether is produced while the formation of olefinic oligomer by-product is reduced.

The process of the invention results in a reduction in the selectivity of olefin dimer formation in alkyl tert-alkyl ether production while enhancing the selectivity of the formation of tert-alkyl ether.

DETAILED DESCRIPTION OF THE INVENTION

Typical feedstock materials for etherification reactions according to the present invention include olefinic streams, such as FCC light cracked gas containing butene isomers, often in mixture with substantial amounts of propene, propane, n-butane and isobutane. The $C_4$ components usually contain a major amount of unsaturated compounds, such as 10–35% isobutylene, 20–55% linear butenes, and small amounts of butadiene. Also, C$_4$+ heavier olefinic hydrocarbon streams may be used, particularly mixtures of isobutylene and isoamylene. These aliphatic streams are produced in a variety of petroleum refinery operation such as catalytic cracking of gas oil or the like. Suitable alkanol reactants for etherification include lower aliphatic C$_1$–C$_4$ primary or secondary alcohols, particularly dry methanol. The dry methanol feedstream should preferably have a purity of about 99.8 wt %.

The reaction of methanol with isobutylene and isoamylenes at moderate conditions with a resin catalyst is known technology, as provided by R. W. Reynolds, et al., *The Oil and Gas Journal*, Jun. 16, 1975, and S. Pecci and T. Floris, *Hydrocarbon Processing*, December, 1977. Preferred catalysts include polymeric sulfonic acid exchange resin such as Amberlyst 15. However, it has been found, as previously noted, that acidic zeolite catalyst can be advantageously used in the etherification of iso-olefins with alkanol. Effective catalysts include zeolite Beta and ZSM-5.

In the etherification process it is known that alkanol and iso-olefins may be reacted in equimolar quantities or either reactant may be in molar excess to influence the complete conversion of the other reactant. Because etherification is an incomplete reaction the etherification effluent comprises unreacted alkanol and unreacted hydrocarbons. On a stoichiometric equivalencies basis, equimolar quantities of methanol and iso-olefins are advantageous but an excess between 2 and 250% of either component can be passed to the etherification reaction unit. In the present invention, the molar ratio of alkanol to iso-olefin, such as methanol to iso-butylene, can be between about 0.7 and 2, but preferably the molar ratio is 1 for methanol to isobutylene. Advantageously, the excess methanol may be about 40% or more when the hydrocarbon feedstream comprises significant quantity of isoamylenes, but equimolar quantities are preferred when the hydrocarbon feedstream consists essentially of the more reactive iso-butene.

In the presence of acidic catalysts, particularly zeolite catalyst, some olefin dimerization occurs during etherification. This side reaction lowers the selectivity of the process for the production of tertiary alkyl ether. If ether of high purity is desired, dimer formation in any significant quantity also necessitates a distillation step to separate the dimer, or higher oligomers, from tertiary alkyl ether product. If a large excess of alkanol is used to retard the formation of dimer, recovery of the unreacted alkanol also requires a costly distillation and/or extraction step. The present invention describes a method to overcome the dilemma and provide a process that exhibits higher selectivity for tertiary alkyl ether, at the expense of process selectivity for the formation of dimer or higher oligomer by-product.

Iso-olefins or isoalkenes in this invention are those having the formula R$_2$C=CH$_2$ or R$_2$C=CHR. Alkanols which may be used in the present invention include methanol, ethanol, 1-propanol, isopropanol, 1-butanol, 2-butanol and isobutanol. Alkyl tert-alkyl ethers produced through the process of the present invention include MTBE, TAME, ethyl tertiary butyl ether, ethyl tertiary amyl ether, n-propyl tertiary butyl ether, n-propyl tertiary amyl ether, isopropyl tertiary butyl ether, isopropyl tertiary amyl ether, n-butyl tertiary butyl ether, n-butyl tertiary amyl ether, sec-butyl tertiary butyl ether, sec-butyl tertiary amyl ether, and the like.

The zeolite etherification catalysts preferred for use herein include the crystalline aluminosilicate zeolites having a silica to alumina ratio of at least 12, a constraint index of about 1 to 12 and acid cracking activity greater than 20, preferably about 30 to 300, and most preferably 50 to 250. Representative of the ZSM-5 type zeolites are ZSM-5, ZSM-11, ZSM-23, ZSM-35, and ZSM-48. ZSM-5 is disclosed and claimed in U.S. Pat. No. 3,702,886 and U.S. Pat. No. Re. 29,948; ZSM-11 is disclosed and claimed in U.S. Pat. No. 3,709,979. Also, see U.S. Pat. No. 4,076,842 for ZSM-23; U.S. Pat. No. 4,016,245 for ZSM-35. The disclosures of these patents are incorporated herein by reference.

In general, the useful catalysts embrace two categories of zeolite, namely, the intermediate pore size variety as represented, for example, by ZSM-5, which possess a Constraint Index of greater than about 2 and the large pore variety as represented, for example, by zeolites Y and Beta, which possess a Constraint index no greater than about 2. Both varieties of zeolites will possess a framework silicato-alumina ratio of greater than about 7.

A convenient measure of the extent to which a zeolite provides controlled access to molecules of varying sizes to its internal structure is the aforementioned Constraint Index of the zeolite. A zeolite which provides relatively restricted access to, and egress from, its internal structure is characterized by a relatively high value for the Constraint Index, i.e., above about 2. On the other hand, zeolites which provide relatively free access to the internal zeolitic structure have a relatively low value for the Constraint Index, i.e., about 2 or less. The method by which Constraint Index is determined is described fully in U.S. Pat. No. 4,016,218, to which reference is made for details of the method.

Constraint Index (CI) values for some zeolites which can be used in the process of this invention are:

| Zeolite | Constraint Index (At Test Temperature, °C.) |
|---|---|
| ZSM-4 | 0.5 (316) |
| ZSM-5 | 6–8.3 (371–316) |
| ZSM-11 | 5–8.7 (371–316) |
| ZSM-20 | 0.5 (371) |
| ZSM-35 | 4.5 (454) |
| ZSM-38 | 2 (510) |
| ZSM-48 | 3.5 (538) |
| ZSM-50 | 2.1 (427) |
| TMA Offretite | 3.7 (316) |
| TEA Mordenite | 0.4 (316) |
| Clinoptilolite | 3.4 (510) |
| Mordenite | 0.5 (316) |
| REY | 0.4 (316) |
| Amorphous Silica-Alumina | 0.6 (538) |
| Dealuminized Y | 0.5 (510) |
| Zeolite Beta | 0.6–2.0 (316–399) |

The large pore zeolites which are useful as catalysts in the process of this invention, i.e., those zeolites having a Constraint Index of no greater than about 2, are well known to the art. Representative of these zeolites are zeolite Beta, zeolite X, zeolite L, zeolite Y, ultrastable zeolite Y (USY), dealuminized Y (Deal Y), rare earth-exchanged zeolite Y (REY), rare earth-exchanged dealuminized Y (RE Deal Y), mordenite, ZSM-3, ZSM-4, ZSM-20, and ZSM-50 and mixtures of any of the foregoing. Although zeolite Beta has a Constraint Index of about 2 or less, it should be noted that this zeolite does not behave exactly like other large pore zeolites.

However, zeolite Beta does satisfy the requirements for a catalyst of the present invention.

Zeolite Beta is described in U.S. Re. Pat. No. 28,341 (of original U.S. Pat. No. 3,308,069), to which reference is made for details of this catalyst.

In practicing the etherification process of the present invention, it can be advantageous to incorporate the zeolite(s) into some other material, i.e., a matrix or binder, which is resistant to the temperature and other conditions employed in the process. Useful matrix materials include both synthetic and naturally-occurring substances, e.g., inorganic materials such as clay, silica and/or metal oxides. Such materials can be either naturally-occurring or can be obtained as gelatinous precipitates or gels including mixtures of silica and metal oxides. The zeolite(s) employed herein can be composited with a porous matrix material such as carbon alumina, titania, zirconia, silica, silica-alumina, silica-magnesia, silica-zirconia, silica-thoria, silica-beryllia, silica-titania, etc., as well as ternary oxide composition, such as silica-alumina-thoria, silica-aluminazirconia, silica-alumina-magnesia, silica-magnesia-zirconia, etc. The matrix can be in the form of a cogel. The relative proportions of zeolite component(s) and matrix material, on an anhydrous basis, can vary widely with the zeolite content ranging from between 1 to about 99 wt %, and more usually in the range of about 5 to about 90 wt % of the dry composite. In some cases, it may be advantageous to provide the zeolite etherification catalyst(s) in the form of an extrudate bound with a low acidity refractory oxide binder. The minimum dimension of the catalyst particle is preferably 1/32 to ¼ inch.

The zeolite(s) selected for use herein will generally possess an alpha value after steaming or hydrothermal treatment of at least about 10, preferably at least 30 and more preferably at least about 50. "Alpha value", or "alpha number", is a measure of zeolite acidic functionality and is more fully described together with details of its measurement in U.S. Pat. No. 4,016,218, *J. Catalysis*, 6, pp. 278–287 (1966) and *J. Catalysis*, 61, pp. 390–396 (1980). The procedure outlined in the latter reference (1980) has been used to determine the alpha values cited in this invention. Zeolites of low acidity (alpha values of less than about 300) can be achieved by steaming or hydrothermal treatment. In the case of steaming, the zeolite(s) can be exposed to steam at elevated temperatures ranging from about 500° F. to about 1200° F. and preferably from about 750° F. (260° C.) to about 1000° F. (538° C.). This treatment can be accomplished in an atmosphere of 100% steam or an atmosphere consisting of steam and a gas which is substantially inert to the zeolite. A similar treatment can be accomplished at lower temperatures employing elevated pressure, e.g., at from about 350° F. (177° C.) to about 700° F. (371° C.) with from about 10 to about 200 atmospheres. Specific details of several steaming procedures may be gained from the disclosures of U.S. Pat. Nos. 4,325,994; 4,374,296; and 4,418,235, the contents of which are incorporated by reference herein.

The present invention concerns the discovery that pretreatment by steaming or hydrothermal treatment of the zeolite catalyst, particularly zeolite Beta catalyst, selectively reduces the rate of oligomerization compared to that of etherification in the process for the production of alkyl tert-alkyl ethers. Thus, the yield of oligomer is considerably reduced with only a smaller effect on the yield of ether. Further, it is believed that aging will also be improved by a pretreatment comprising steaming or hydrothermally treating zeolite Beta catalyst in the etherification process.

Preferably, the invention provides an improvement of zeolite Beta catalyst as used for the synthesis of ethers from alcohols and olefins; most specifically with the improvement of Beta catalyst for MTBE and/or TAME synthesis from methanol and isobutene and/or amylene. Selectivity to ether products compared to olefin oligomerization products is improved. Catalyst aging is projected to improve as well. The improvement is accomplished by pretreating the catalyst by steaming, i.e., gaseous water at elevated temperatures, or by hydrothermal treatment employing liquid water at elevated temperature. The improvement particularly applies to catalytic particles comprising Beta zeolite crystals, which may include binder material such as alumina, silica, zirconia, titania, carbon, etc. The improvement most particularly applies to extruded zeolite Beta containing catalyst bound with alumina or zirconia. The improvement is effective when olefins (e.g. $C_4$ olefin mixtures, $C_5$ olefin mixtures, $C_4$–$C_5$ olefin mixtures, or $C_4$–$C_8$ olefin mixtures) are etherified with a monohydric $C_1$ to $C_5$ alcohol, or mixtures, as described above.

Improvement of the catalyst by steam treatment is accomplished by contacting the zeolite Beta catalyst particles with steam at elevated temperature. Temperatures above 300° C. can be used but those above 400° C. are preferred, with temperatures above 450° C. particularly preferred. Steam pressures of above about 0.1 atmosphere are utilized, with 0.5 to 5 atm preferred, and 0.8 to 2 atm particularly preferred. Contacting times of from several minutes to days are used, with 1 to 50 hrs preferred, and 2 to 24 hrs particularly preferred. Higher steam pressures and temperatures are associated with shorter treatment times. Successful steaming results in a zeolite alpha value that is about 80% of the untreated zeolite, or lower. Steaming to give an alpha value of 10% to 75% of the untreated zeolite is preferred, or alpha values as indicated above.

Improvement of the catalyst by hydrothermal treatment is accomplished by contacting zeolite Beta catalyst particles with liquid water at elevated temperatures. Temperatures above 100° C. can be used with temperatures above 125° C. preferred and temperatures above 150° C. particularly preferred. Treatment pressure must be high enough to maintain liquid water. Contact times of from several hours to several days are used. Higher temperatures are associated with shorter treatment times. Successful hydrothermal treatment results in a zeolite alpha value that is about 80% of the untreated zeolite, or lower. Hydrothermal treatment to give an alpha value of 10% to 75% of the untreated zeolite is preferred, or alpha values as indicated above.

In the following Examples A to E, various zeolite Beta catalysts were investigated for etherification selectivity. Each Example contains five or six experiments carried out under varying conditions of temperature, WHSV, etc. as shown. Examples A and B employ a zeolite Beta catalyst that has not been subjected to selectivating pretreatment by either steaming or liquid water at elevated temperature. The catalyst in Example A is alumina bound while the catalyst in B is zirconia bound. Examples C and D use a zeolite Beta catalyst that has been pretreated by steaming under the conditions shown. The catalyst in Example C and D is zirconia bound, but the catalyst in Example D has been steamed for 24 hrs. Example E employs zirconia bound zeolite Beta that has been hydrothermally treated with liquid water at 160° C. and 1000 psig (7000 kPa) for 3 days. The general test conditions and procedure are described below and tabulated in Table I along with results.

EXAMPLES A-E

Test Reaction: A feed of 2 moles methanol to 1 mole isobutene is converted in a ⅜-inch tubular fixed bed reactor operated at 100° C. and 200 psig. About 0.3 g catalyst is diluted with sand to a constant bed volume of 8 ml. Feed rates are varied within the range of 10 to 300 WHSV (olefin based on zeolite). Isobutene conversion and selectivity are determined at each feed rate covering the range of 50 to 80% conversion. Selectivity, S, is the weight fraction dimer in the combined dimer and ether product.

Selectivations: Catalyst were steamed in a stream of about 100% steam at atmospheric pressure at the indicated temperature and times. Catalyst was hydrothermally selectivated by contacting with water in a high pressure vessel for the time, temperature and pressure indicated.

TABLE I

EXAMPLE A
Alumina Bound Zeolite Beta (65%) 1/16 inch Extrudate
No Selectivating Treatment, Alpha = 360

| RUN. No. | 1 | 2 | 3 | 4 | 5 | 6 |
|---|---|---|---|---|---|---|
| HR ON STREAM | 2 | 6 | 24 | 27 | 30 | 31 |
| TEMPERATURE, °C. | 101 | 100 | 100 | 100 | 100 | 100 |
| PRESSURE, kPa | 1400 | 1400 | 1400 | 1400 | 1400 | 1400 |
| MOLES MEOH/OLE | 1.94 | 1.94 | 1.56 | 1.98 | 1.87 | 2.01 |
| WHSV | 104.15 | 69.43 | 7.85 | 22.11 | 53.58 | 209.06 |
| CONVERSION MEOH | 25.5 | 29.0 | 52.0 | 41.0 | 33.6 | 13.4 |
| ISOBUTENE | 46.3 | 57.6 | 85.9 | 83.5 | 66.8 | 25.5 |
| PRODUCT COMPOSITION, WT PCT | | | | | | |
| MTBE | 98.41 | 93.35 | 92.18 | 88.87 | 91.90 | 97.92 |
| HC | 1.59 | 6.65 | 7.82 | 11.13 | 8.10 | 2.08 |
| ERROR MB WT PCT | 5 | 1 | 14 | −2 | 2 | 9 |

EXAMPLE B
Zirconia Bound Zeolite Beta (70%) 1/16 inch Extrudate
No Selectivating Treatment, alpha = 380

| RUN NO. | 7 | 8 | 9 | 10 | 11 | 12 |
|---|---|---|---|---|---|---|
| HR ON STREAM | 2 | 5 | 22 | 25 | 28 | 28 |
| TEMPERATURE, °C. | 102 | 101 | 99 | 101 | 101 | 101 |
| PRESSURE, kPa | 1400 | 1400 | 1400 | 1400 | 1400 | 1400 |
| MOLES MEOH/OLE | 1.94 | 1.93 | 1.88 | 1.98 | 1.92 | 1.97 |
| WHSV | 92.28 | 62.21 | 7.26 | 20.39 | 47.42 | 191.47 |
| CONVERSION MEOH | 26.8 | 31.9 | 39.9 | 37.6 | 32.7 | 14.4 |
| ISOBUTENE | 62.5 | 65.5 | 86.4 | 82.1 | 69.0 | 27.2 |
| PRODUCT COMPOSITION, WT PCT | | | | | | |
| MTBE | 87.99 | 88.76 | 87.12 | 85.98 | 86.16 | 97.90 |
| HC | 12.01 | 11.24 | 12.88 | 14.02 | 13.84 | 2.10 |
| ERROR MB WT PCT | 7 | 0 | 6 | −1 | 0 | 2 |

EXAMPLE C
Zirconia Bound Zeolite Beta (70%) 1/16 inch Extrudate
Selectivation: Steamed at 900° F. (482° C.) & 1 atm for 8 hr.
Alpha = 115

| RUN NO. | 13 | 14 | 15 | 16 | 17 |
|---|---|---|---|---|---|
| HR ON STREAM | 3 | 5 | 23 | 26 | 27 |
| TEMPERATURE, °C. | 101 | 101 | 99 | 101 | 108 |
| PRESSURE, kPa | 1400 | 1400 | 1400 | 1400 | 1400 |
| MOLES MEOH/OLE | 1.87 | 1.85 | 2.70 | 2.14 | 1.87 |
| WHSV | 39.71 | 26.00 | 2.47 | 8.03 | 83.43 |
| CONVERSION MEOH | 37.1 | 42.5 | 46.0 | 40.1 | 28.6 |
| ISOBUTENE | 72.5 | 78.2 | 91.3 | 92.2 | 54.4 |
| PRODUCT COMPOSITION, WT PCT | | | | | |
| MTBE | 92.94 | 94.91 | 88.83 | 89.79 | 93.22 |
| HC | 7.06 | 5.09 | 11.17 | 10.21 | 6.78 |
| ERROR MB WT PCT | 3 | −1 | 6 | −1 | 3 |

EXAMPLE D
Zirconia Bound Zeolite Beta (70%) 1/16 inch Extrudate
Selectivation: Steamed at 900° F. (482° C.) & 1 atm for 24 Hr.
Alpha = 71

| RUN NO. | 18 | 19 | 20 | 21 | 22 | 23 |
|---|---|---|---|---|---|---|
| HR ON STREAM | 2 | 6 | 23 | 26 | 27 | 29 |
| TEMPERATURE, °C. | 99 | 100 | 99 | 100 | 100 | 101 |
| PRESSURE, kPa | 1400 | 1400 | 1400 | 1400 | 1400 | 1400 |
| MOLES MEOH/OLE | 1.96 | 1.89 | 1.96 | 1.88 | 1.94 | 2.63 |
| WHSV | 36.92 | 25.73 | 2.87 | 8.11 | 18.88 | 67.27 |
| CONVERSION MEOH | 37.7 | 43.9 | 42.2 | 38.7 | 40.5 | 26.7 |
| ISOBUTENE | 68.9 | 61.9 | 89.2 | 89.4 | 83.0 | 48.3 |
| PRODUCT COMPOSITION, WT PCT | | | | | | |
| MTBE | 96.44 | 96.24 | 88.70 | 86.80 | 92.22 | 98.31 |
| HC | 3.56 | 3.76 | 11.30 | 13.20 | 7.78 | 1.69 |
| ERROR MB WT PCT | 4 | −8 | 29 | 14 | 4 | 4 |

EXAMPLE E

TABLE I-continued

Zirconia Bound Zeolite Beta (70%) 1/16 inch Extrudate
Selectivation: Hydrothermal Treatment at 160° C. & 1000
psig for 3 days
Alpha = 250

| RUN NO. | 24 | 25 | 26 | 27 | 28 | 29 |
|---|---|---|---|---|---|---|
| HR ON STREAM | 2 | 5 | 21 | 24 | 26 | 27 |
| TEMPERATURE, °C. | 102 | 101 | 100 | 101 | 102 | 101 |
| PRESSURE, kPa | 1400 | 1400 | 1400 | 1400 | 1400 | 1400 |
| MOLES MEOH/OLE | 1.98 | 1.87 | 1.98 | 1.86 | 1.76 | 1.94 |
| WHSV | 48.35 | 33.00 | 3.55 | 10.29 | 25.94 | 99.71 |
| CONVERSION MEOH | 30.0 | 36.4 | 44.8 | 41.3 | 31.0 | 8.4 |
| ISOBUTENE | 52.9 | 60.6 | 83.7 | 81.4 | 52.9 | 15.5 |
| PRODUCT COMPOSITION, WT PCT | | | | | | |
| MTBE | 96.68 | 97.87 | 92.20 | 90.47 | 93.93 | 99.19 |
| HC | 3.32 | 2.13 | 7.80 | 9.53 | 6.07 | 0.81 |
| ERROR MB WT PCT | 1 | 3 | 2 | −1 | 1 | 2 |

To show the effect of catalyst treatment on selectivity at constant severity, values of S were plotted against butene conversion, where s is the weight fraction of dimer in the combined dimer and ether product. The plot was used to interpolate selectivity at 70% conversion. This value is tabulated in Table II.

TABLE II

Effect of Treatment on Dimer Selectivity at a Severity of 70% Isobutene Conversion (at conditions of test reaction)

| EXAMPLE | SELECTIVITIES (wt %) | |
|---|---|---|
| | DIMER | ETHER |
| Selectivity Without Treatment | | |
| A. Untreated Alumina bound Beta (65%) 1/16 in. Extrudate. Alpha = 360 or 100% of untreated alpha value. | 9 | 91 |
| B. Untreated Zirconia bound Beta (70%) 1/16 in. Extrudate. Alpha = 390 or 100% of untreated alpha value. | 12 | 88 |
| Selectivity Improved by Treatment | | |
| C. Catalyst of Example B Steamed 900° F., (482° C.) for 1 atm, 8 hr. Alpha = 115 or 29% of untreated alpha value. | 5 | 95 |
| D. Catalyst of Example B Steamed 900° F, (482° C.) for 1 atm, 24 hr. Alpha = 71 or 18% of untreated alpha value. | 5 | 96 |
| E. Catalyst of Example B Hydrotreated, 160° C., 3 day (1000 psig). Alpha = 250 or 64% of untreated alpha value. | 5 | 95 |

Comparing the untreated Examples A and B with the treated Examples C, D and E, Table II clearly shows that ether selectivity is improved by steaming or hydrothermal treatment of zeolite Beta catalyst.

Although the present invention has been described with preferred embodiments, it is to be understood that modifications and variations may be resorted to, without departing from the spirit and scope of this invention, as those skilled in the art will readily understand. Such modifications and variations are considered to be within the purview and scope of the appended claims.

What is claimed is:

1. A process for reducing the formation of olefinic oligomer by-products and improving tertiary ether selectivity in the production of high octane alkyl tertiary alkyl ether employing acid zeolite beta catalyst particles having alpha value greater than 300, comprising:
   steaming or hydrothermally treating said zeolite catalyst particles at elevated temperature to provide treated acid zeolite beta catalyst particles having a reduced alpha value of less than 300; and
   contacting alkanol and a hydrocarbon feedstream rich in iso-olefins with said steamed or hydrothermally treated catalyst particles under iso-olefin etherification conditions sufficient to provide at least 70 weight percent conversion of said iso-olefins, whereby a product containing at least 95 weight percent of said alkyl tertiary alkyl ether is produced while the formation of olefinic oligomer by-product is not more than 5 weight percent.

2. The process of claim 1 wherein said steaming is carried out at a temperature above about 300° C., a contact time of at least three minutes at a steam pressure above 0.1 atmospheres.

3. The process of claim 2 wherein said temperature is above 400° C., said contact time is between 1 and 50 hours at a steam pressure between about 0.5 and 5 atmospheres.

4. The process of claim 2 wherein said temperature is above 450° C., said contact time is between 2 and 25 hours at a steam pressure between about 0.8 and 2 atmospheres.

5. The process of claim 1 wherein said acid zeolite catalyst particles are hydrothermally treated with liquid water at a temperature above 100° C., a contact time of at least three hours at a pressure sufficient to maintain said water in a liquid phase.

6. The process of claim 5 wherein said temperature is above 125° C.

7. The process of claim 5 wherein said temperature is above 150° C. and said contact time is between 3 and 96 hours.

8. The process of claim 1 wherein said acid zeolite catalyst particles comprise zeolite crystals containing a binder.

9. The process of claim 8 wherein said catalyst comprises extruded zeolite containing alumina or zirconia binder.

10. The process of claim 1 wherein said alkanol comprises $C_1$–$C_5$ alkanol.

11. The process of claim 1 wherein said alkanol includes methanol, ethanol, n-propanol, isopropanol or mixtures thereof.

12. The process of claim 1 wherein said hydrocarbon feedstream comprises $C_4$–$C_8$ hydrocarbons rich in iso-olefins.

13. The process of claim 12 wherein said iso-olefins comprise isobutene, isoamylene or mixtures thereof.

14. The process of claim 1 wherein said alkanol comprises methanol, said iso-olefin comprises isobutene and said alkyl tertiary alkyl ether comprises methyl tertiary butyl ether.

15. The process of claim 1 wherein said alkyl tertiary alkyl ether comprises methyl tertiary amyl ether.

16. In the process for the production of methyl tertiary butyl ether comprising contacting methanol and isobutene with acid zeolite Beta catalyst particles under iso-olefins etherification conditions, said catalyst having an alpha value greater than 300, the improvement comprising:

pretreating said catalyst particles with steam or liquid water at elevated temperature to provide acid catalyst particles having alpha value less than 300, whereby the formation of olefin oligomer by-product under said etherification conditions is reduced.

17. The process of claim 16 wherein said pretreatment with steam is carried out at a temperature above 300° C., a contact time of at least three minutes at a steam pressure above 0.1 atmospheres.

18. The process of claim 16 wherein said pretreatment with liquid water is carried out at a temperature above about 100° C., a contact time of at least three hours at a pressure sufficient to maintain said water in a liquid phase.

19. The process of claim 1 wherein said reduced alpha value of said treated catalyst is not greater than 80% of untreated catalyst.

20. The process of claim 1 wherein said treated catalyst has an alpha value between 10% and 75% of the untreated zeolite.

21. A process for the production of high octane value alkyl tertiary butyl and/or tertiary amyl ether with improved ether selectivity over oligomer, comprising:

contacting alkanol and a hydrocarbon feedstream rich in isobutene and/or isoamylene with pretreated zeolite beta catalyst under etherification conditions sufficient to provide at least 70 wt % conversion of said isobutene and/or isoamylene, whereby a product stream is produced containing at least 95 wt % of said ether and not more than 5 wt % of said oligomer; said catalyst having been pretreated by steaming at a temperature above 300° C., a contact time of at least several minutes at a steam pressure above 0.1 atmosphere, or hydrothermally pretreated with liquid water at a temperature above 100° C., a contact time of at least several hours at a pressure sufficient to maintain said water in liquid phase.

22. The process of claim 21 wherein said alkanol is selected from the group consisting of methanol, ethanol, 1-propanol, isopropanol, 1-butanol, 2-butanol, isobutanol and mixtures thereof.

23. The process of claim 21 wherein said pretreatment by steaming is carried out a temperature above 400° C., said contact time is between 1 and 50 hours at a steam pressure between 0.5 and 5 atmospheres.

24. The process of claim 23 wherein said temperature is above 450° C., said contact time is between 2 and 25 hours at a steam pressure between 0.8 and 2 atmospheres.

25. The process of claim 21 wherein said pretreatment with liquid water is carried out at a temperature above 125° C.

26. The process of claim 25 wherein said temperature is above 150° C. and said contact time is between several hours and several days.

27. The process of claim 21 wherein said alkyl tertiary butyl ether comprises methyl tertiary butyl ether.

28. The process of claim 21 wherein said alkyl tertiary amyl ether comprises methyl tertiary amyl ether.

* * * * *